(12) United States Patent
Yip et al.

(10) Patent No.: US 9,889,220 B1
(45) Date of Patent: Feb. 13, 2018

(54) AIR FRESHENER ENHANCER WITH IMPROVED AIR FLOW AND WITH HEIGHT ADJUSTABLE STAND

(71) Applicant: Hometek International Ltd., Fo Tan (HK)

(72) Inventors: Po Chun Yip, Tsuenwan (HK); Kwok Kuen Tong, Sha Tin (HK)

(73) Assignee: Hometek International Ltd., Fo Tan (HK)

( * ) Notice: Subject to any disclaimer, the term of this patent is extended or adjusted under 35 U.S.C. 154(b) by 92 days.

(21) Appl. No.: 15/173,059

(22) Filed: Jun. 3, 2016

(51) Int. Cl.
*A61L 9/12* (2006.01)
*B01F 3/04* (2006.01)

(52) U.S. Cl.
CPC ............... *A61L 9/122* (2013.01); *B01F 3/04* (2013.01); *A61L 2209/133* (2013.01); *A61L 2209/15* (2013.01)

(58) Field of Classification Search
CPC .......... A61L 9/12; B01F 3/04; B01F 3/04085
USPC ............... 261/30, DIG. 88; 422/124; 239/60
See application file for complete search history.

(56) References Cited

U.S. PATENT DOCUMENTS

2005/0191217 A1  9/2005  Selander
2012/0181350 A1* 7/2012  Snider .................... A61L 9/048
                                                         239/34

FOREIGN PATENT DOCUMENTS

CN          103861142 A     6/2014

* cited by examiner

*Primary Examiner* — Robert A Hopkins
(74) *Attorney, Agent, or Firm* — Richard M. Goldberg

(57) ABSTRACT

An air freshener enhancer includes a base having a support for holding a fragrance composition, first inlet openings for receiving ambient air, first outlet openings positioned adjacent the fragrance composition, and main airflow channels for supplying air from the first inlet openings to the first outlet openings; a fan for blowing the air from the first inlet openings, through the main airflow channels and out through the first outlet openings; and the base further includes second inlet openings in a side wall for receiving ambient air, second outlet openings positioned above the fragrance support, and auxiliary airflow channels positioned between the main airflow channels and extending between the second inlet openings and second outlet openings such that air forced through the main airflow channels results in suction of air through the auxiliary airflow channels and out the second outlet openings into contact with the fragrance composition.

22 Claims, 14 Drawing Sheets

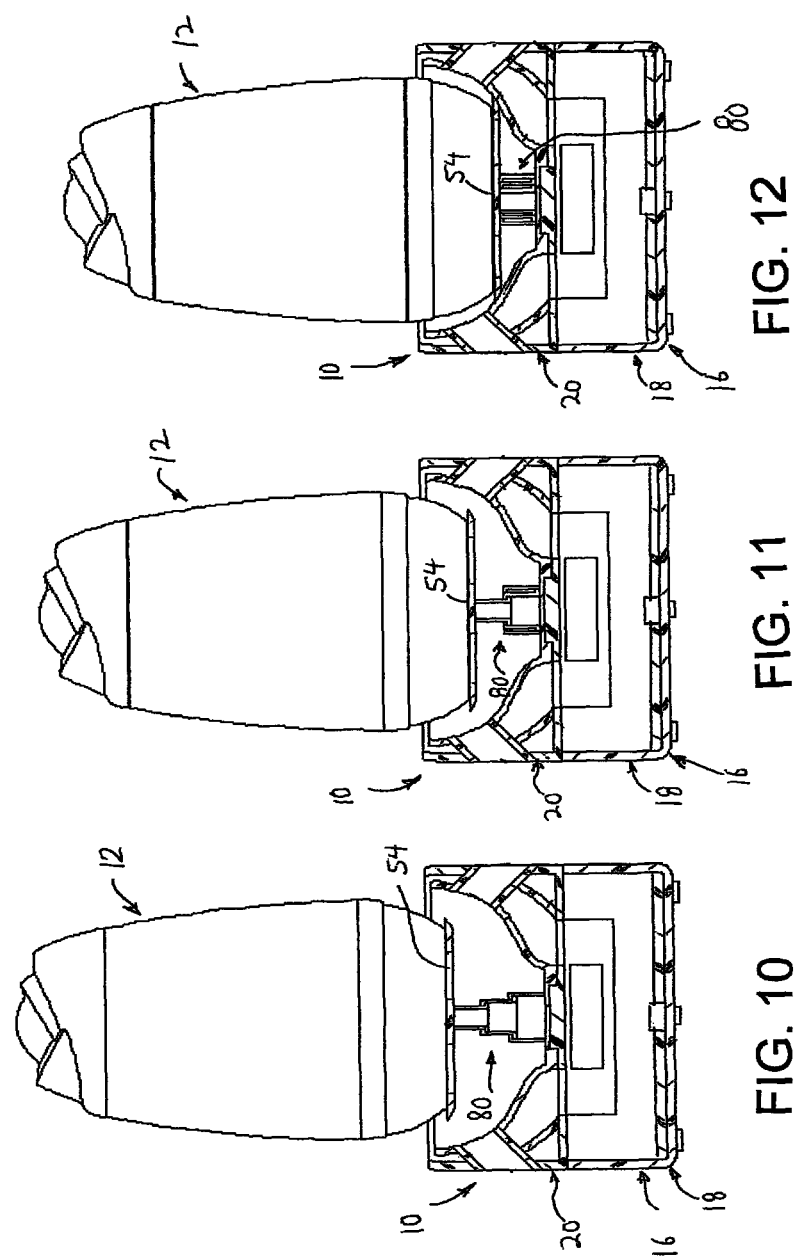

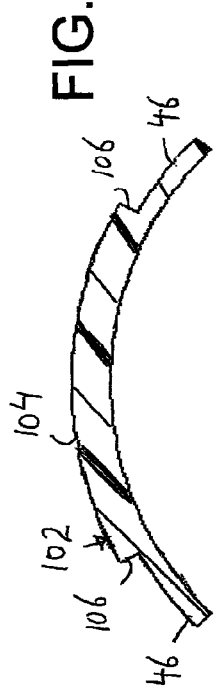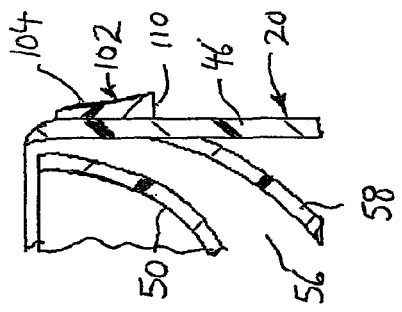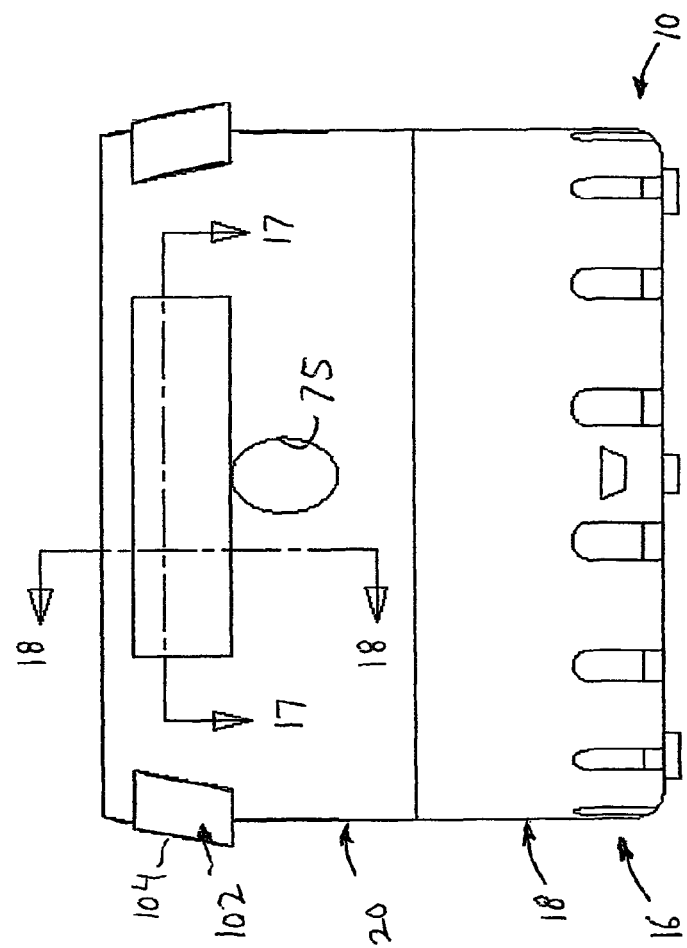

AIR FRESHENER ENHANCER WITH IMPROVED AIR FLOW AND WITH HEIGHT ADJUSTABLE STAND

BACKGROUND OF THE INVENTION

The present invention relates generally to air fresheners, and more particularly, is directed to an air freshener enhancer with improved air flow and with a height adjustable stand.

Room air fresheners which emit fragrant scents into a room in order to freshen the air and mask or neutralize odors, are well known in the art. These air fresheners generally provide a liquid, oil, gel or solid in a container, which when opened or vented to atmosphere, release the fragrance in an amount depending upon the extent that the openings or vents are opened.

However, in an enclosed room, there is little air flow, so that emitting and dispensing of the fragrance throughout the room is very slow and inefficient.

Air fresheners are known that use fans to aid in the dispersion of the fragrance throughout the room. For example, see U.S. Patent Publication No. 2005/0191217. See also Chinese Patent Publication No. CN 103861142A. However, the air freshener composition and the fan are fixed in a housing. Therefore, adjustment of the direction of the flow is not possible.

Also, with such air fresheners, since the fan and air freshener composition are fixed in the housing at the point of sale, an entirely new unit must be purchased to provide a different scented air freshener composition after its depletion.

It would also be desirable to provide an air freshener enhancer with a fan that can be used with different existing air fresheners. However, because each manufacturer provides a different configuration and height of its air freshener, and thereby a different positioning of the openings or vents associated with the air freshener composition therewithin, this is not possible.

It would also be desirable to provide adjustment of the forced air exiting the housing to impinge on the air freshener composition at different positions.

SUMMARY OF THE INVENTION

Accordingly, it is an object of the present invention to provide an air freshener enhancer that overcomes the aforementioned problems.

It is another object of the present invention to provide an air freshener enhancer with a height adjustable stand for accommodating different commercially available air fresheners with fragrance compositions at different heights.

It is still another object of the present invention to provide an air freshener enhancer having improved air flow around the air freshener.

It is yet another object of the present invention to provide an air freshener enhancer in which air flow from a fan over the air freshener is increased.

It is yet another object of the present invention to provide an air freshener enhancer in which air flow from a fan over the air freshener is directionally and/or height controlled.

In accordance with an aspect of the present invention, an air freshener enhancer includes a base having a fragrance support for holding an exposable fragrance composition, first inlet openings for receiving ambient air, first outlet openings positioned adjacent the exposable fragrance composition, and main airflow channels for supplying ambient air from the first inlet openings to the first outlet openings. A fan is mounted in the base for blowing the ambient air from the first inlet openings, through the main airflow channels and out through the first outlet openings. The base further includes second inlet openings in a side wall of the base for receiving ambient air, second outlet openings positioned above the fragrance support, and auxiliary airflow channels positioned between adjacent main airflow channels and extending between the second inlet openings and second outlet openings in a manner such that air forced through the main airflow channels results in suction of ambient air through the auxiliary airflow channels and out the second outlet openings into contact with the exposable fragrance composition.

Preferably, the auxiliary airflow channels are oriented crosswise to the main airflow channels.

The base includes a hollow lower base section having a lower end with the first input openings therein, a hollow upper base section mounted on top of the lower section, the upper base section including a bottom wall having third openings therein, the side wall having the second inlet openings, and wherein the fan is mounted to the bottom wall of the upper base section and extends into the hollow lower base section, wherein the main airflow channels are connected between the third openings and the second outlet openings, and wherein the auxiliary airflow channels are positioned in the upper base section.

The fragrance support includes a cup-shaped wall mounted in the base and including a fragrance support plate for mounting the exposable fragrance composition thereon. Preferably, the cup-shaped wall partially defines the main airflow channels, and the second outlet openings extend through the cup-shaped wall.

There is also a closing arrangement for at least partially closing the first inlet openings. The closing arrangement includes a movable plate positioned over the first inlet openings and having openings which can be positioned either in alignment with the first inlet openings to maintain the first inlet openings in a fully open position, partially in alignment with the first inlet openings to maintain the first inlet openings in a partially open position, or completely out of alignment with the first inlet openings to completely close the first inlet openings.

In accordance with another aspect of the present invention, an air freshener enhancer includes a base including a fragrance support for holding an exposable fragrance composition, first inlet openings for receiving ambient air, first outlet openings positioned adjacent the exposable fragrance composition, and main airflow channels for supplying ambient air from the first inlet openings to the first outlet openings; a fan mounted in the base for blowing the ambient air from the first inlet openings, through the main airflow channels and out through the first outlet openings; and a height adjustment arrangement mounted in the base and connected with the fragrance support for adjusting the height of the fragrance support.

Preferably, the height adjustment arrangement includes a plurality of telescoping, nested tube supports connected between the fragrance support and a wall of the base, and a locking arrangement for locking each tube support in an extended or retracted position with respect to another tube support. The locking arrangement includes recesses in the tube supports and beads in adjacent tube supports for engaging in the recesses to lock the tube supports in the extended or retracted position thereof.

The fragrance support includes a fragrance support plate on which the exposable fragrance composition is adapted to be mounted and which is connected with one of the tube supports. In one embodiment, finger openings are provided in the plate for grasping by a person to adjust the height of the fragrance support plate via the height adjustment arrangement. In another embodiment, a graspable member is connected to the fragrance support plate for grasping by a person to adjust the height of the fragrance support plate via the height adjustment arrangement.

In accordance with still another aspect of the present invention, an air freshener enhancer includes a base including a fragrance support for holding an exposable fragrance composition, first inlet openings for receiving ambient air, first outlet openings positioned adjacent the exposable fragrance composition, and main airflow channels for supplying ambient air from the first inlet openings to the first outlet openings; a fan mounted in the base for blowing the ambient air from the first inlet openings, through the main airflow channels and out through the first outlet openings; and air reflectors mounted on the base adjacent the first outlet openings for adjusting a position at which the forced air exits the base.

Preferably, the base includes a plurality of mounting arrangements at an upper end thereof, and the air reflectors are movably mounted on the mounting arrangements. Each mounting arrangement includes a mounting block secured to an outer surface of a sidewall of the base, and each air reflector is slidably mounted up and down on a respective mounting block, with each air reflector including an upper opening. Each mounting block includes an outwardly and downwardly extending outer surface and side surfaces, and each air reflector includes a thin walled member having an outer wall mounted over the outer surface of the mounting block and side walls mounted over the side surfaces of the mounting block.

In accordance with yet another aspect of the present invention, an air freshener enhancer includes a base including a fragrance support for holding an exposable fragrance composition, first inlet openings for receiving ambient air, first outlet openings positioned adjacent the exposable fragrance composition, and main airflow channels for supplying ambient air from the first inlet openings to the first outlet openings; a fan mounted in the base for blowing the ambient air from the first inlet openings, through the main airflow channels and out through the first outlet openings; and a cover which seats upon an upper end of the base, the cover including an air directional arrangement for directing forced air from the first outlet openings to the exposable fragrance composition in order to provide fragrance entrained air, and cover openings for permitting escape of the fragrance entrained air.

The cover openings are preferably arranged around a 360° circle so as to permit escape of the fragrance entranced air in all directions. The cover includes a central domed wall including the cover openings, an annular wall surrounding the central domed wall, the annular wall including the air directional arrangement, and an annular retaining wall connected with the annular wall for mounting the cover on the upper end of the base. In one embodiment, the air directional arrangement is formed by the annular wall having a convex shape which redirects the entrained air from the first outlet openings to the exposable fragrance composition. In another embodiment, the air directional arrangement is formed by at least one curved deflector which redirects the entrained air from the first outlet openings to the exposable fragrance composition.

In another embodiment, there is an annular collar positioned between the cover and the upper and of the base for extending the height of the cover relative to the base to enable receipt on the support of a large exposable fragrance composition.

In accordance with a further aspect of the present invention, an air freshener enhancer includes a base having a fragrance support for holding an exposable fragrance composition, first inlet openings for receiving ambient air, first outlet openings positioned adjacent the exposable fragrance composition, and main airflow channels for supplying ambient air from the first inlet openings to the first outlet openings. A fan is mounted in the base for blowing the ambient air from the first inlet openings, through the main airflow channels and out through the first outlet openings. A height adjustment arrangement is mounted in the base and connected with the fragrance support for adjusting the height of the fragrance support. The base further includes second inlet openings in a side wall of the base for receiving ambient air, second outlet openings positioned above the fragrance support, and auxiliary airflow channels positioned between adjacent main airflow channels and extending between the second inlet openings and second outlet openings in a manner such that air forced through the main airflow channels results in suction of ambient air through the auxiliary airflow channels and out the second outlet openings into contact with the exposable fragrance composition. An outlet air adjustment arrangement is formed by either air reflectors mounted on the base adjacent the first outlet openings for adjusting a position at which the forced air exits the base, or a cover which seats upon an upper end of the base, the cover including an air directional arrangement for directing forced air from the first outlet openings to the exposable fragrance composition in order to provide fragrance entrained air, and cover openings for permitting escape of the fragrance entrained air.

The above and other features of the invention will become readily apparent from the following detailed description thereof which is to be read in connection with the accompanying drawings.

BRIEF DESCRIPTION OF THE DRAWINGS

FIG. 10 is a cross-sectional view similar to FIG. 7, with the height adjustment arrangement in its fully extended position;

FIG. 11 is a cross-sectional view similar to FIG. 7, with the height adjustment arrangement in an intermediate extended position;

FIG. 12 is a cross-sectional view similar to FIG. 7, with the height adjustment arrangement in its fully retracted position;

FIG. 16 is a front elevational view of the air freshener enhancer of FIG. 14, with the air reflectors removed;

FIG. 17 is a cross-sectional view of the further modified air freshener enhancer of FIG. 16, taken along line 17-17 thereof;

FIG. 18 is a cross-sectional view of the further modified air freshener enhancer of FIG. 16, taken along line 18-18 thereof;

DETAILED DESCRIPTION

Figure 1:
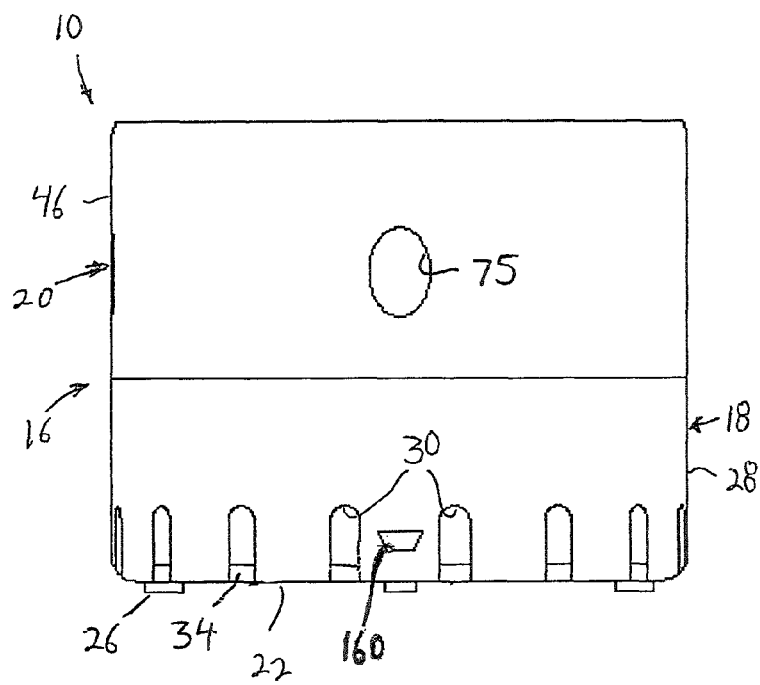
FIG. 1 is a front elevational view of an air freshener enhancer according to the present invention.

Referring to the drawings in detail, and initially to FIG. 1-6, there is shown an air freshener enhancer 10 with a fan that can be used with different existing air fresheners 12 having exposable fragrance compositions 14. Air freshener enhancer 10 includes a base 16 having a lower base section 18 and an upper base section 20 which is connected to and seats on top of lower base section 18.

Lower base section 18 is hollow and includes a bottom base plate 22 that supports air freshener enhancer 10 on a surface. Although base plate 22 is shown to have a circular shape, base plate 22 can have any suitable shape, for example, square, rectangular, triangular, etc. A plurality of, for example, sixteen, elongated, radially directed slot openings 24 extend inwardly from the outer periphery of base plate 22 for a length, for example, equal to about one-fifth of the diameter of base plate 22.

Rubber feet 26 are provided on the underside of base plate 22 to raise base plate 22 up from its supporting surface in order to allow the flow of air through slot openings 24. In addition, rubber feet 26 prevent marring of the surface and inhibit sliding movement of base plate 22 on the supporting surface. Rubber feet 26 are positioned between some adjacent slot openings 24.

Lower base section 18 further includes a circumferential side wall 28 which extends upwardly from the outer periphery of base plate 22 and preferably has the same outer shape as base plate 22, although the present invention is not limited thereto. A plurality of, for example, 16, elongated, slot openings 30 extend upwardly from the lower edge of circumferential side wall 28 and are in open communication with slot openings 24 and extend for a length, for example, equal to about one-third of the height of circumferential side wall 28.

Figures 2, 3:
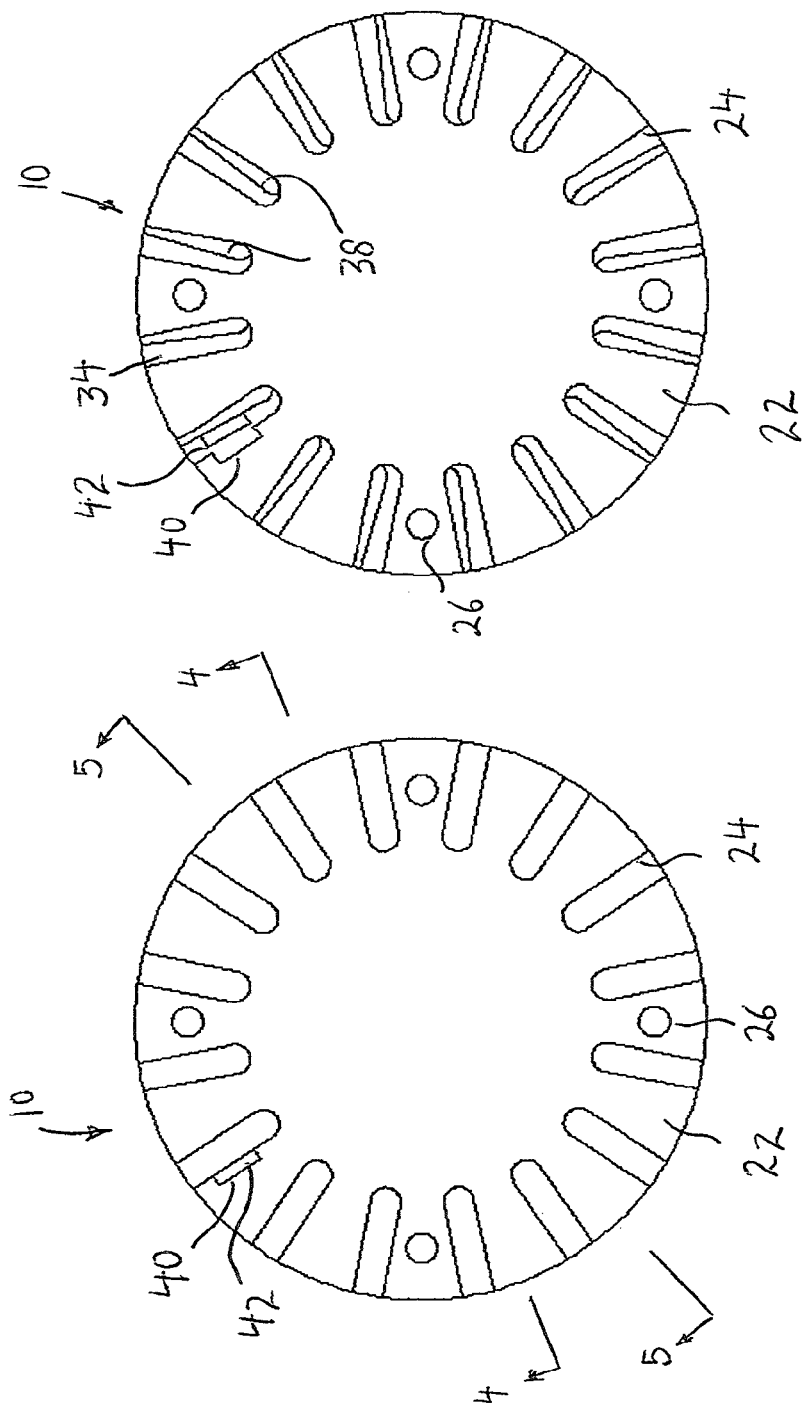
FIG. 2 is a bottom plan view of the air freshener enhancer of FIG. 1, with the bottom openings fully open.
FIG. 3 is a bottom plan view of the air freshener enhancer of FIG. 1, with the bottom openings one-third open.
Figure 4:
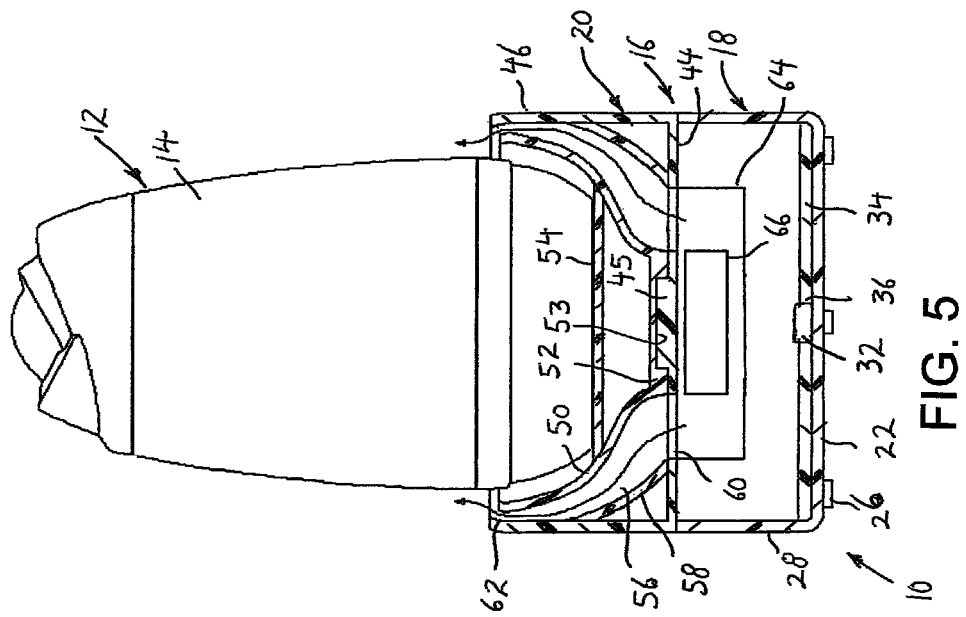
FIG. 4 is a cross-sectional view of the air freshener enhancer of FIG. 2, taken along line 4-4 thereof, showing an existing air freshener positioned thereon.
Figure 5:
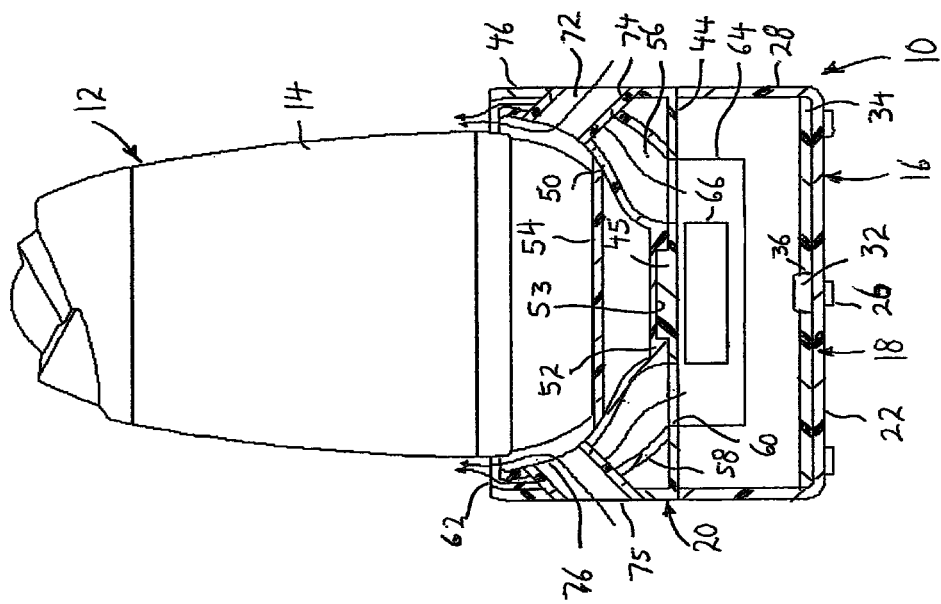
FIG. 5 is a cross-sectional view of the air freshener enhancer of FIG. 2, taken along line 5-5 thereof, showing an existing air freshener positioned thereon.

As shown in FIGS. 4 and 5, a central post 32 extends upwardly from the center of the upper surface of base plate 22. A circular closure plate 34 includes a central opening 36 that receives central post to rotatably mount closure plate 34 on top of base plate 22. Closure plate 34 includes a plurality of, for example, sixteen slot openings 38 which correspond to slot openings 24 as to position, shape and dimensions. Thus, when slot openings 38 are in full alignment with slot openings 24, as shown in FIG. 2, slot openings 24 are fully open. However, when closure plate 34 is rotated relative to base plate 22, slot openings 24 can be fully or partially closed by closure plate 34. FIG. 3 shows slot openings 24 being about one-third of its fully open position. In order to rotate closure plate 34, one slot opening 24 includes a side opening 40 and closure plate 34 includes a tab 42 that extends downwardly through the respective slot opening 24. When tab 42 is fully located within the side opening 42, as shown in FIG. 2, slot openings 24 are fully open and when tab 42 is moved to the opposite side of the respective slot opening 24, all slot openings 24 are fully closed by closure plate 34. It will be appreciated that closure plate 38 partially blocks the lower end of slot openings 30 in circumferential side wall 28.

Upper base section 20 is hollow and includes a bottom base plate 44. Although base plate 44 is shown to have a circular shape, base plate 44 can have any suitable shape, for example, square, rectangular, triangular, etc. Preferably, base plate 44 has the same shape and dimensions as circumferential side wall 28 of lower base section 18, and sits on the upper edge thereof. Preferably, base plate 44 is fixedly secured to the upper edge of circumferential side wall 28 by any suitable means, such as adhesive, welding or the like. A boss 45 is centrally positioned on the upper surface of base plate 44.

Upper base section 20 further includes a circumferential side wall 46 which extends upwardly from the outer periphery of base plate 44 and preferably has the same outer shape as base plate 44, although the present invention is not limited thereto.

A cup-shaped annular inner wall 50 extends upwardly and outwardly from a central hub 52 which includes a lower recess 53 that receives boss 45 at the center of the upper surface of base plate 44. The upper edge of cup-shaped annular inner wall 50 is positioned slightly lower than and slightly inwardly from circumferential side wall 46, such that cup-shaped annular inner wall 50 tapers in diameter from the upper end to the lower end thereof. A fragrance support plate 54 is connected to the upper exposed surface of cup-shaped annular inner wall 54 for supporting existing air freshener 12 thereon, with the majority of air freshener 12 extending upwardly out of air freshener enhancer 10 above circumferential side wall 46.

A circumferential main airflow channel 56 is formed in upper base section 20 between circumferential side wall 46 and cup-shaped annular inner wall 50. Main airflow channel 56 is formed with a circumferential wall 58 that connects with the outer surface of cup-shaped annular inner wall 50. Base plate 44 includes a circumferential opening 60 or a plurality angularly spaced apart openings 60 arranged about central boss 45 and which are in open fluid communication with the lower end of main airflow channel 56. A circumferential opening 62 is formed at the upper end of main airflow channel 56. In this manner, air can flow inwardly through slot openings 24 and 30 in lower base section 18, upwardly through opening 60 in base plate 44, through main airflow channel 56 and out through opening 62, which is at a position corresponding to the lower end of the fragrance composition 14, such as a fragrance gel in air freshener 12 in order to vaporize the air freshener material to carry it throughout the room.

Alternatively, a plurality of, for example, four, main airflow channels 56, openings 60 and openings 62 can equiangularly be formed in place of their circumferential counterparts.

Figure 6:
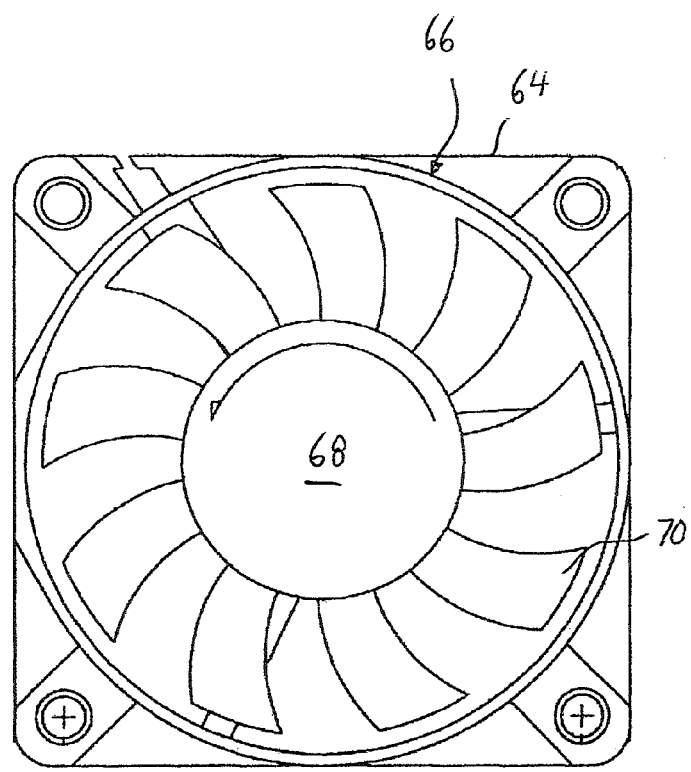
FIG. 6 is an enlarged plan view of the fan in the air freshener enhancer of FIG. 1.

A fan housing 64 is centrally secured to the underside of base plate 44 and includes a fan 66 having a fan motor 68 with radially extending fan blades 70, as best shown in FIG. 6. Power to fan motor 68 is supplied via an electrical cord (not shown) which can be plugged into a conventional socket. With this arrangement, rotation of fan blades 70 causes air to be sucked up through slot openings 24 and 30 and forced out through opening 62. As a result, the forced air flows over the fragrance composition 14 in order to carry the fragrance throughout the room.

In accordance with an aspect of the present invention, as shown in FIG. 4, auxiliary airflow channels 72 are formed in upper base section 20. Specifically, each airflow channel 72 is formed of an annular wall 74 which opens at one end through a lower opening 75 in circumferential side wall 46 and opens at the opposite end through an upper opening 76 in cup-shaped annular inner wall 50 at a position slightly below the upper end thereof. Auxiliary airflow channels 72 are spaced at positions so as to extend through main airflow channel 56 and are angled upwardly from circumferential side wall 46 toward cup-shaped annular inner wall 50. It will be appreciated that auxiliary airflow channels 72 are oriented across main airflow channel 56 at approximately a right angle, although the present invention is not limited thereby. Thus, as fan 66 forces air out through opening 62, a pressure differential is created which results in additional air being sucked up through auxiliary airflow channels 72 in order to increase the flow of air over exposable fragrance composition 14.

It will be appreciated that, in the embodiment of FIGS. 1-6, fragrance support plate 54 is positioned at a fixed height on cup-shaped annular inner wall 50 so as to accommodate a specific air freshener 12. However, it may be desirable to adjust the height of fragrance support plate 54 to accommodate air fresheners 12 of different dimensions and shapes.

Referring now to FIGS. 7-12, there is shown a modification of the first embodiment which includes a height adjustment arrangement 78 formed by a plurality of nested, telescoping tube supports 80, with the lower end of the outermost tube support 80a having the largest diameter and being fixed on top of the central hub 52, and the upper end of the innermost tube support 80c having the smallest diameter being fixed to the underside of fragrance support plate 54. An intermediate tube support 80b is telescopically connected between tube supports 80a and 80c.

In this regard, outermost tube support 80a is formed with an annular side wall 82a, the lower end of which is fixed to the upper surface of central hub 52, and an upper inwardly directed annular restraining wall 84a. The inner surface of annular side wall 82a is formed with an upper annular recess 86a at a position immediately below annular restraining wall 84a, and a lower annular recess 87a at a position immediately above the lowermost edge of annular side wall 82a.

Intermediate tube support 80b includes an annular side wall 82b having an outer diameter substantially equal to or slightly less than the inner diameter of annular restraining wall 84a, and an upper inwardly directed annular restraining wall 84b. The inner surface of annular side wall 82b is formed with an upper annular recess 86b at a position immediately below annular restraining wall 84b, and a lower annular recess 87b at a position immediately above the lowermost edge of annular side wall 82b. In addition, intermediate tube support 80b includes a lower outwardly directed annular stop wall 88b. Annular stop wall 88b has an outer diameter substantially equal to or slightly less than the inner diameter of annular side wall 82a. An annular bead 90b is formed on the outwardly facing surface of annular stop wall 88b. Thus, in the fully lowered position of intermediate tube support 80b, as shown in FIGS. 11 and 12, annular bead 90b fits within lower annular recess 87a, while in the fully raised position, shown in FIGS. 9 and 10, annular bead 90b fits within upper annular recess 86a in order to lock intermediate tube support 80b relative to outermost tube support 80a.

Innermost tube support 80c includes an annular side wall 82c having an outer diameter substantially equal to or slightly less than the inner diameter of annular restraining wall 84b, and a lower outwardly directed annular stop wall 88c. Annular stop wall 88c has an outer diameter substantially equal to or slightly less than the inner diameter of annular side wall 82b. An annular bead 90c is formed on the outwardly facing surface of annular stop wall 88c. Thus, in the fully lowered position, annular bead 90c fits within lower annular recess 87b, while in the fully raised position, annular bead 90c fits within upper annular recess 86b in order to lock innermost tube support 80c relative to intermediate tube support 80b.

In order to move height adjustment arrangement 78 to either the fully extended position shown in FIG. 10 in which all tube supports 80a-80c off fully extended, the intermediate position in which innermost tube support 80c is fully extended and intermediate tube support 80b is retracted into outermost tube support 80a as shown in FIG. 11, or the fully compressed position in which the tube supports 80a-80c are fully nested within each other as shown in FIG. 12, fragrance support plate 54 is provided with two diametrically opposite finger openings 92 which can be grasped by a user to pull innermost tube support 80c upwardly to achieve the positional arrangement of FIG. 10 or 11, or push it downwardly to achieve the positional arrangement of FIG. 12.

Figure 13:
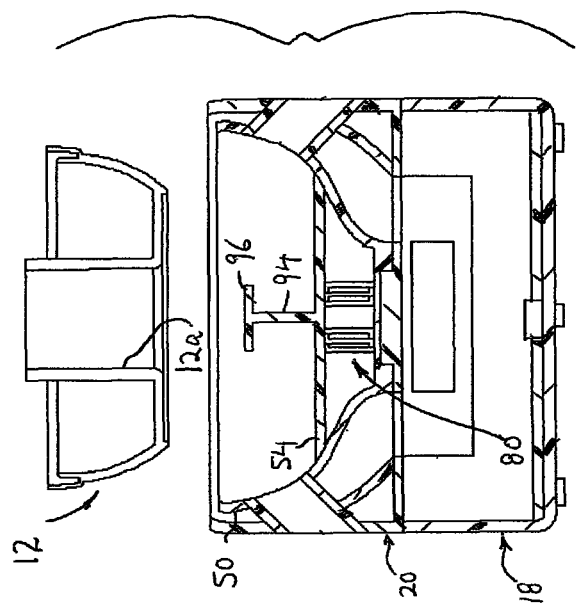
FIG. 13 is a cross-sectional view similar to FIG. 7, of an air freshener enhancer according to a modification of the embodiment of FIG. 7, with a different arrangement for moving the height adjustment arrangement thereof.
Figure 8:
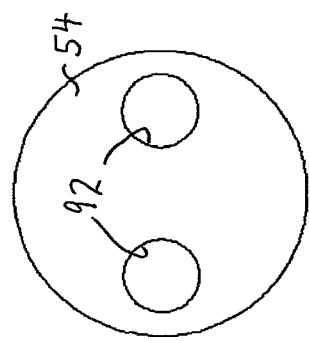
FIG. 8 is a plan view of the fragrance support plate fo the air freshener enhancer of FIG. 7.
Figure 7:
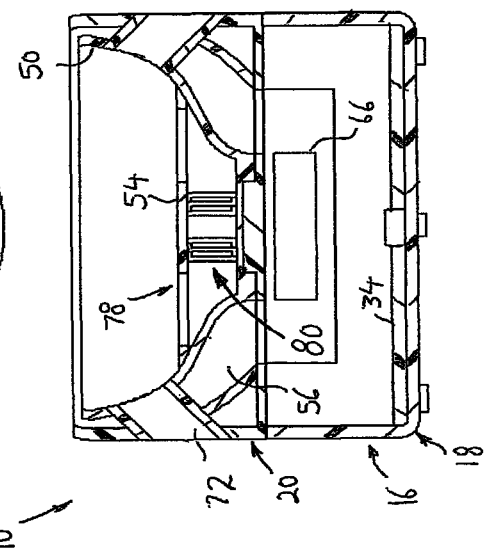
FIG. 7 is a cross-sectional view of an air freshener enhancer according to a modification of the embodiment of FIG. 1.
Figure 9:
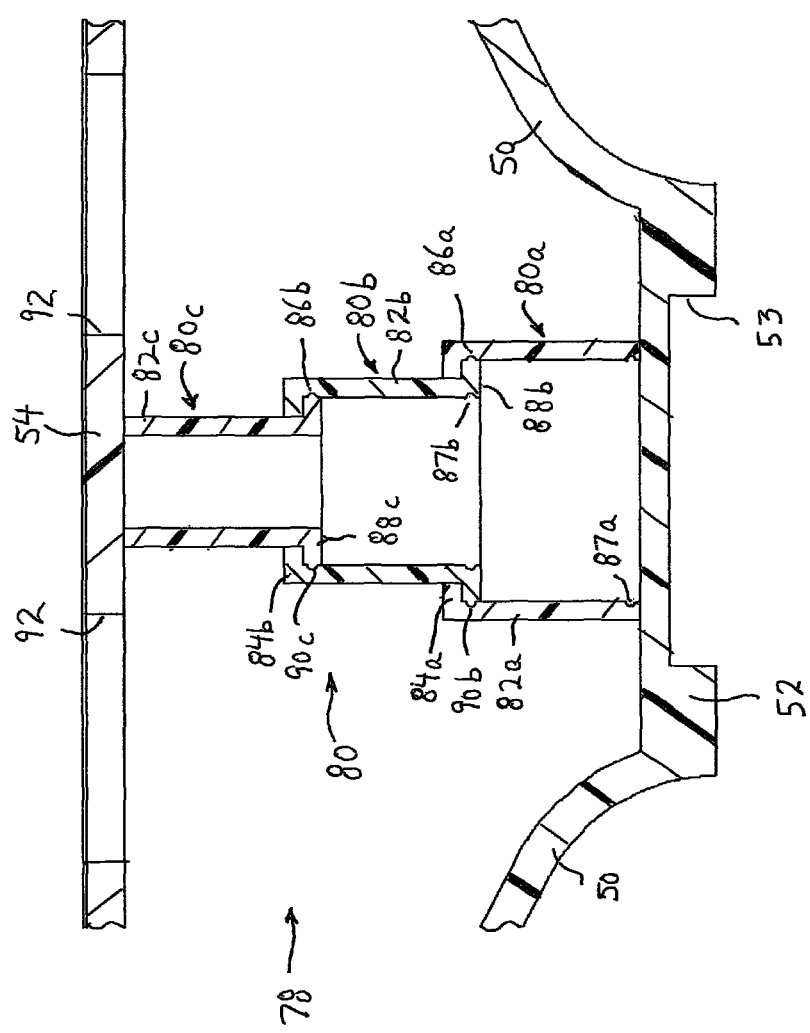
FIG. 9 is an enlarged cross-sectional view of the height adjustment arrangement of the air freshener enhancer of FIG. 7.

Alternatively, as shown in FIG. 13, in place of finger openings 92, a rod 94 can be centrally affixed to the upper surface of fragrance support plate 54 so as to extend upwardly therefrom, with a circular grasping plate 96 secured to the upper and of rod 94 for grasping by a person to pull height adjustment arrangement 78 upwardly or push height adjustment arrangement 78 downwardly. In such case, the lower end of existing air freshener 12 can be formed with a central recess 12*a* through which rod 94 and circular grasping plate 96 can extend when air freshener 12 is seated on top of fragrance support plate 54.

In accordance with another aspect of the present invention, as shown in FIGS. 14-23, air reflectors 100 can be mounted to mounting blocks 102 fixed to the outer surface at the upper end of upper base section 20. Any number of air reflectors 100 and mounting blocks 102 can be provided.

Specifically, mounting blocks 102 are secured in spaced relation around the upper end of circumferential side wall 46. Although mounting blocks 102 are shown to have a substantially trapezoidal shape in sectional view, for example, as shown in FIG. 18, the present invention is not limited thereby. Thus, each mounting block 102 includes an outwardly arcuate surface 104 having a curvature similar to that of the outer surface of circumferential side wall 46, opposite inclined side wall surfaces 106, and a lower wall surface 110, with each mounting block 102 having a generally triangular shape in cross-section. The thickness of each mounting block 102 increase from its upper end to its lower end so that outwardly arcuate surface 104 also slopes outwardly in the downward direction.

Each air reflector 100 is formed with an outer arcuate wall 112 which seats against outwardly arcuate surface 104 and two inwardly inclined side walls 114 which seat against inclined side wall surfaces 106. The upper end of outer arcuate wall 112 is inwardly curved to a small extent only to form an upper limiting wall 116 to limit the downward position of each air reflector 100 on its respective mounting block 102, while still permitting air flow therethrough. In the fully seated position of each air reflector 100, upper limiting wall 116 seats on annular upper wall 48. There is a friction engagement of outer arcuate wall 112 on outwardly arcuate surface 104 and side walls 114 on inclined side wall surfaces 106 at all positions of air reflector 100. In this regard, air reflector 100 is made of a thin walled, flexible and resilient material that enables it to be pushed down over outwardly arcuate surface 104.

Figure 15:
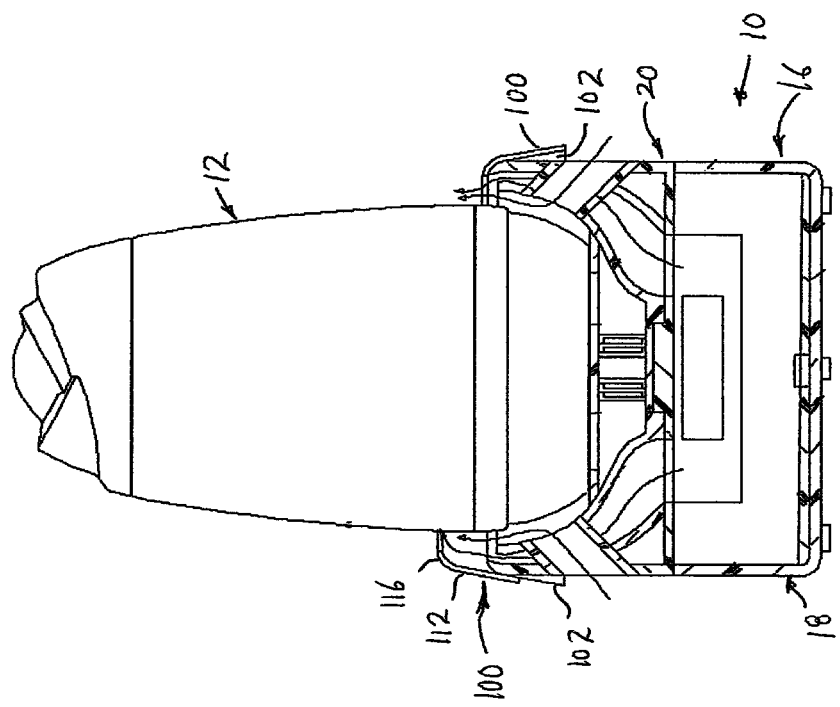
FIG. 15 is a cross-sectional view similar to that of FIG. 4, of the further modified air freshener enhancer of FIG. 14.
Figure 14:
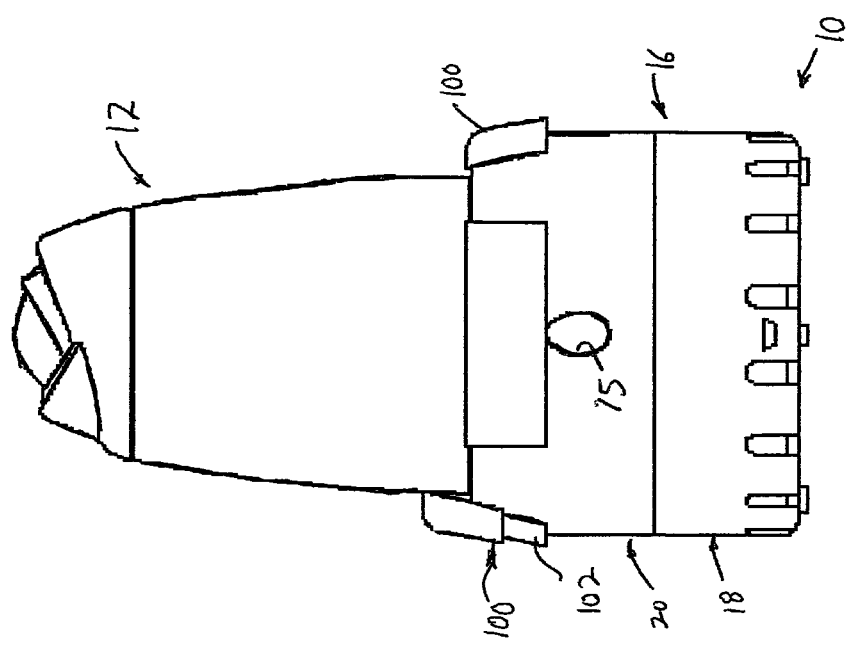
FIG. 14 is an front elevational view of an air freshener enhancer according to a modification of the embodiment of FIG. 1.
Figure 21:
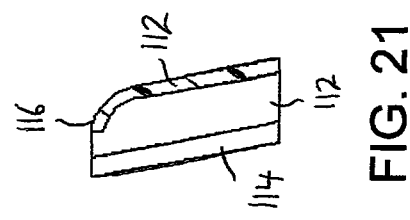
FIG. 21 is a cross-sectional view of the air reflector of FIG. 19, taken along line 21-21 thereof.
Figure 20:
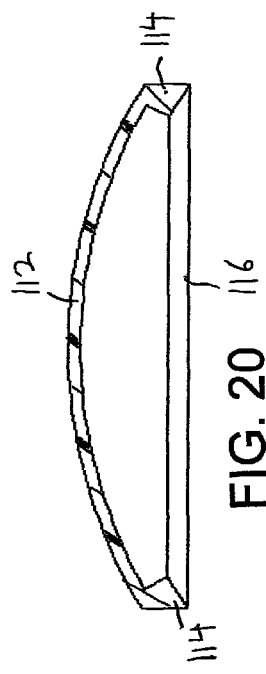
FIG. 20 is a cross-sectional view of the air reflector of FIG. 19, taken along line 20-20 thereof.
Figure 19:
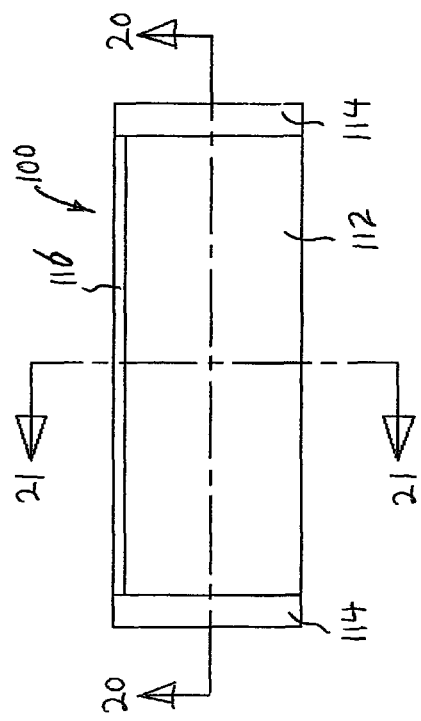
FIG. 19 is a rear elevational view of an air reflector.
Figure 22:
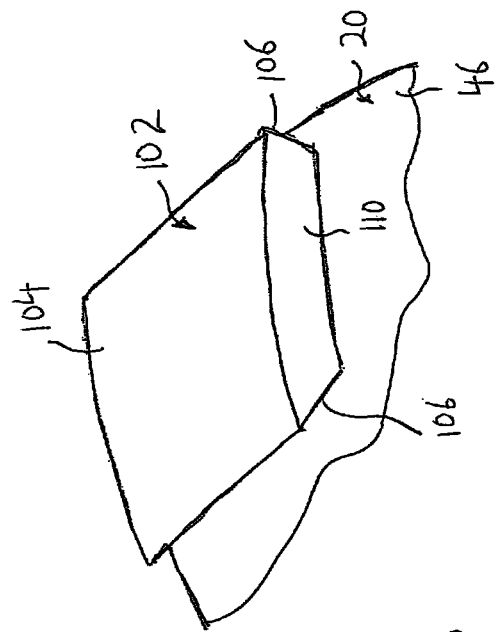
FIG. 22 is a perspective view of a mounting block.
Figure 23:
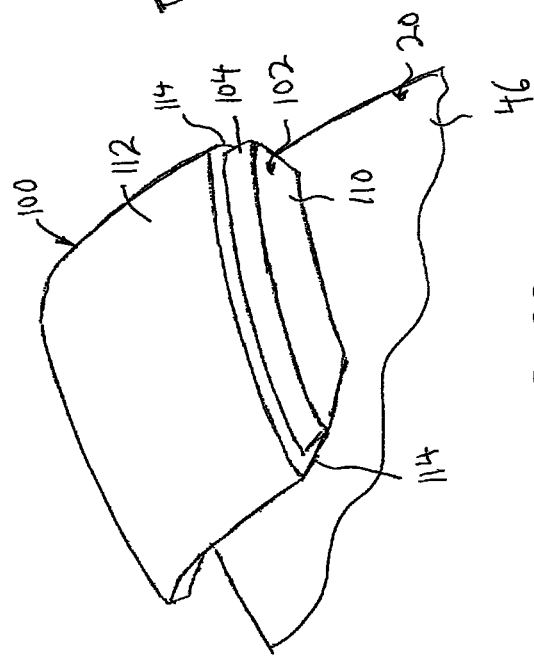
FIG. 23 is a perspective view of an air reflector mounted on a mounting block.

In this manner, each air reflector 100 can be adjusted in height relative to the respective mounting block 102, for example, as shown by the upper position thereof at the left side of FIGS. 14 and 15, and the lower position thereof at the right side of FIGS. 14 and 15, to accommodate different air fresheners 12 in which the exposable fragrance composition 14 thereof is at different heights.

In accordance with another embodiment of the present invention, as shown in FIGS. 24-27, a block 120 of an air freshening material is positioned on fragrance support plate 54 in place of an existing air freshener 12. A cover 122 is positioned on top of upper base section 20 and includes a plurality of openings for enabling escape of the fan forced air which passes over block 120 of the air freshening material.

Specifically, cover 122 includes a central covering wall structure 126 connected to a surrounding annular wall 124. It will be appreciated, however, although the structure 126 is shown to be a domed structure, any suitable shaped structure can be provided.

In a diametric dimension, central domed wall structure 126 preferably extends about one half the diameter of cover 122, while annular wall 124 extends on each side of central domed wall structure 126 for about one quarter the diameter of cover 122, although the present invention is not limited thereto. Further, the height of central domed wall structure 126 is approximately three to four times the height of annular wall 124, although the present invention is not limited thereto. As shown best in FIGS. 26 and 27, central domed wall structure 126 is formed with a plurality of pairs spaced apart, radially extending, parallel, arcuate struts 128 which define openings 130*a* between the struts 128 of each pair and in which each pair of struts 128 is separated from an adjacent pair of struts 128 by generally arcuate triangular openings 130*b*, through which the fragrance can escape. Struts 128 meet at a circular connection 132 at the apex of central domed wall structure 126.

In addition, an annular retaining wall 134 is connected to the outer periphery of annular wall 124 and has an L-shape in cross-section. Retaining wall 134 thereby includes an outwardly extending, horizontal annular wall 136 that seats on top of the edge of circumferential side wall 46, and a downwardly extending, vertical annular wall 138 that rests against the upper end of circumferential side wall 46 with a friction fit, in order to releasably retain cover 122 on top of upper base section 20.

Figure 24:
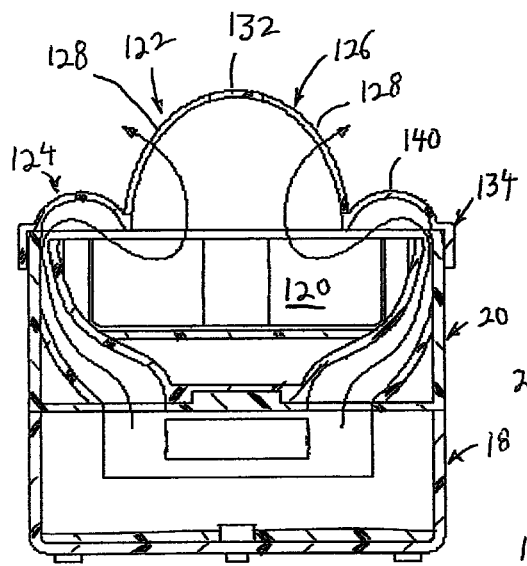
FIG. 24 is a cross-sectional view of an air freshener enhancer according to a still further modification of the embodiment of FIG. 1.
Figure 25:
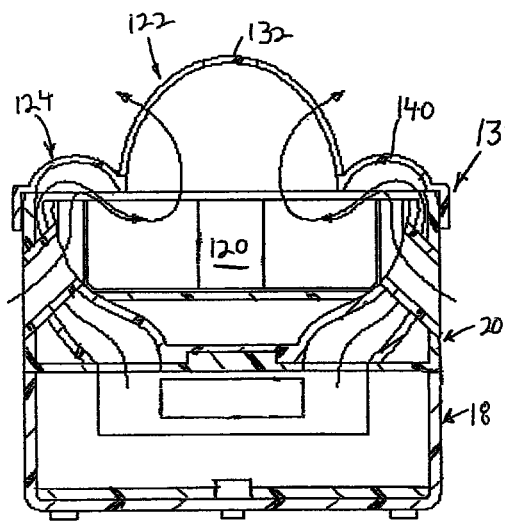
FIG. 25 is a cross-sectional view of the air freshener enhancer of FIG. 24, taken along a different section.
Figure 27:
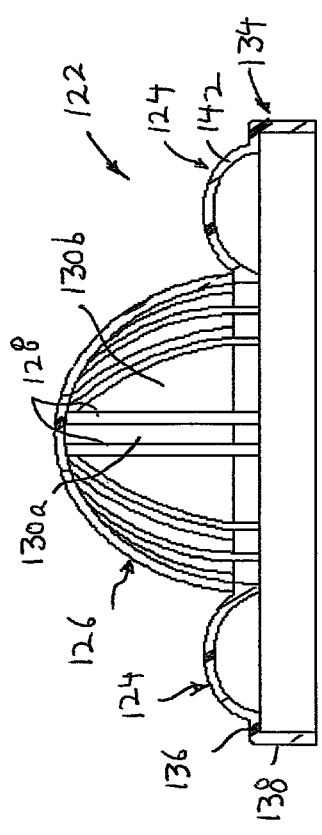
FIG. 27 is a cross-sectional view of the cover of FIG. 26, taken along line 27-27 thereof.

In one embodiment, as shown in FIGS. 24 and 27, annular wall 124 on each side of central domed wall 126 is also formed as a domed or convex wall 140 in cross section.

Figure 28:
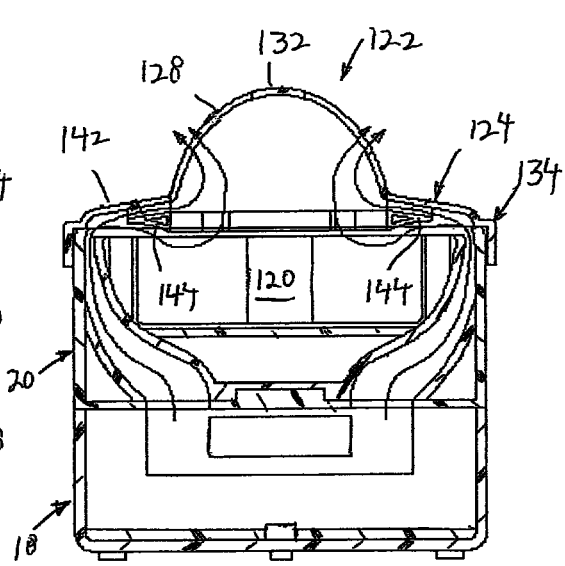
FIG. 28 is a cross-sectional view of an air freshener enhancer according to a modification of the embodiment of FIG. 24.
Figure 29:
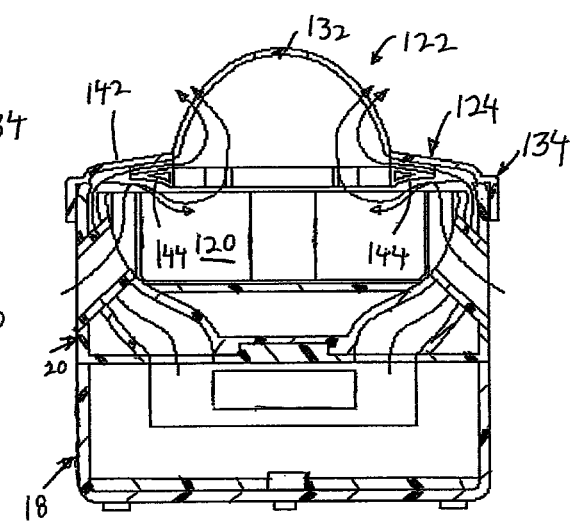
FIG. 29 is a cross-sectional view of the air freshener enhancer of FIG. 28, taken along a different section.
Figure 26:
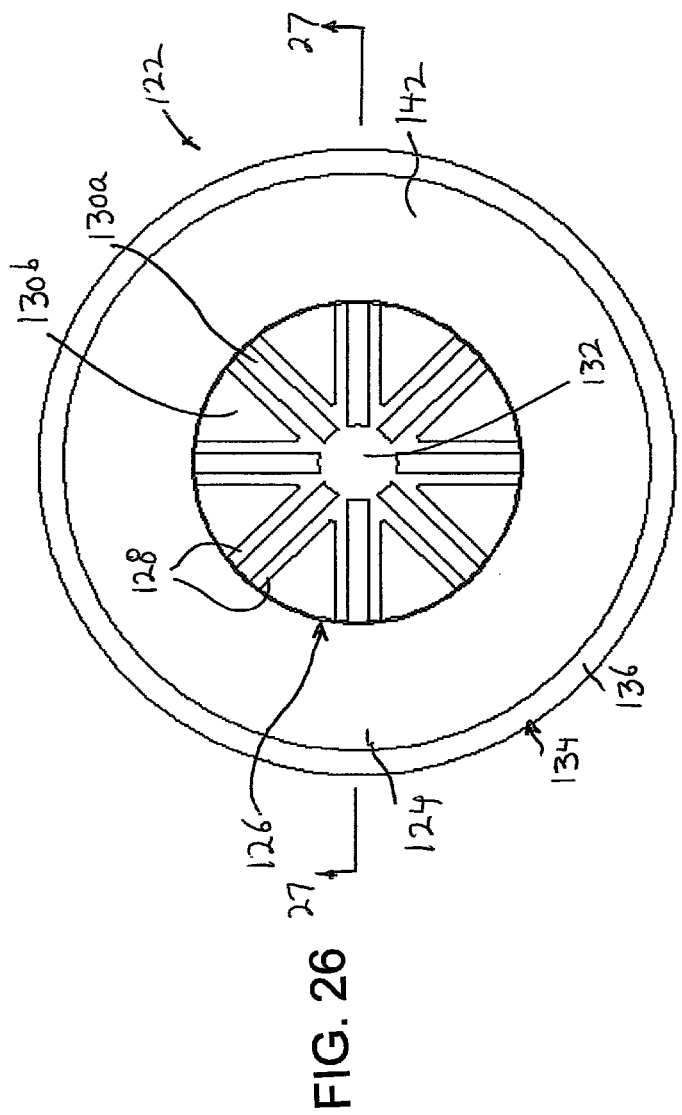
FIG. 26 is a top plan view of the cover of the air freshener enhancer of FIG. 24.

In another embodiment, as shown in FIGS. 28 and 29, annular wall 124 is formed as an annular, downwardly, outwardly sloping wall 142, the inner end of which is connected to central domed wall 126 and the outer end of which is connected to retaining wall 134. Further, the lower end of cover 122 of FIGS. 28 and 29 is formed with an annular curved deflector 144 positioned immediately beneath the inner surface of annular sloping wall 142 where it meets with central domed wall structure 126.

In operation, the air is fan forced out through opening 62, and annular wall 124 (FIGS. 24-27) or annular curved deflector 144 (FIGS. 28 and 29) forces the air downwardly into contact with block 120 of air freshening material where it entrains the air freshening composition and carries it out through openings 130*a* and 130*b* in central domed wall structure 126. Because of the use of central domed wall structure 126, the air exiting through openings 130*a* and 130*b* exits in a 360° manner.

Figure 30:
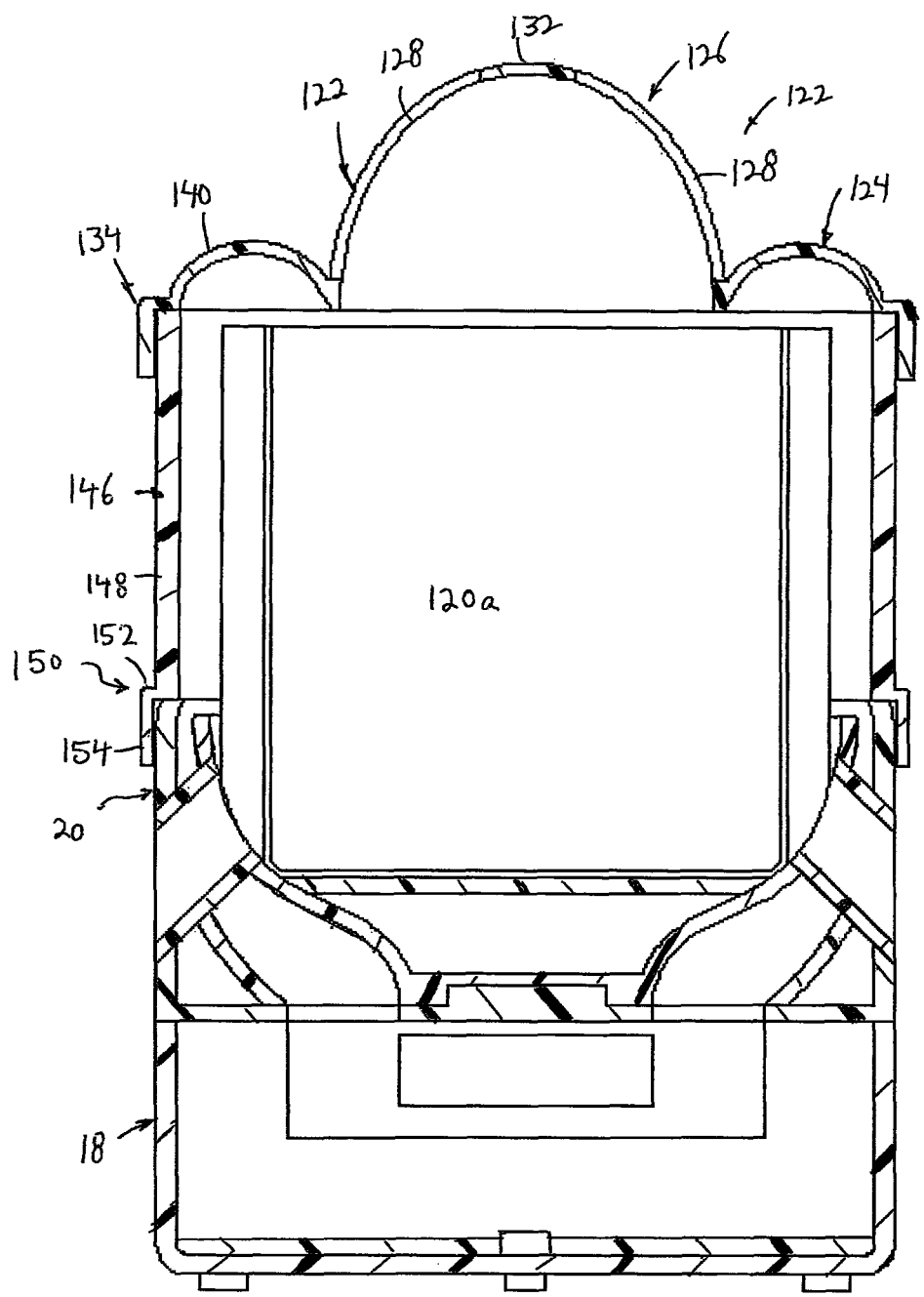
FIG. 30 is a cross-sectional view of an air freshener enhancer according to a further modification of the embodiment of FIG. 24.

As shown in FIG. 30, in order to accommodate a larger block 120*a* of air freshening material, an annular extension collar 146 is provided between upper base section 20 and cover 122. Extension collar 146 includes an annular side wall 148 having a retaining wall 150 connected to the lower and of annular side wall 148, with retaining wall 150 having an L-shape in cross-section. Retaining wall 150 thereby includes an outwardly extending, horizontal annular wall 152 that seats on top of the edge of circumferential side wall 46, and a downwardly extending, vertical annular wall 154 that rests against the side of circumferential side wall 46 with a friction fit, in order to releasably retain extension collar 146 on top of upper base section 20. Cover 122 seats on the upper edge of extension collar 146 in the same manner as previously described.

Figure 31:
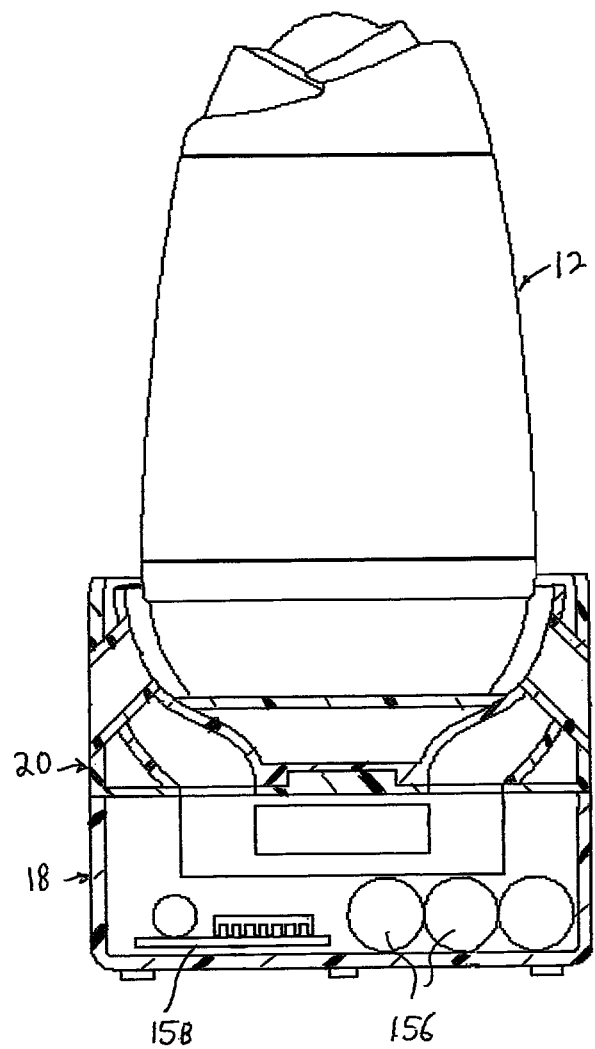
FIG. 31 is a cross-sectional view of an air freshener enhancer according to a yet further modification of the embodiment of FIG. 1.

Lastly, as shown in FIG. 31, in addition to, or as an alternative to the electrical cord (not shown) for powering fan motor 68, a plurality of batteries 156 are provided in lower base section 18. Batteries 156 can be dry batteries or rechargeable batteries, and a connection can be provided for recharging the batteries 156. Circular closure plate 34 is not shown for better illustration only in this figure.

A printed circuit board assembly 158 is also provided in lower base section 18 for controlling various functions. For example, printed circuit board assembly 158 can include a timer circuit for cycling the blowing of air over the fragrance composition during certain times and/or cycles. In addition, printed circuit board assembly 158 can include a circuit for adjusting the speed of fan 66 to one of a predetermined number of speeds or in a variable manner. In this regard, various knobs (not shown) can be provided on base 16 and which are connected to printed circuit board assembly 158 for controlling the fan speeds and the turning on and off of the fan at different times.

In addition, as shown best in FIG. 1, a USB charger port 160 can be provided in lower base section 18 for charging various devices via a USB connection.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

What is claimed is:

1. An air freshener enhancer comprising:
    a base including:
        a fragrance support for holding an exposable fragrance composition,
        first inlet openings for receiving ambient air,
        first outlet openings positioned adjacent the exposable fragrance composition, and
        main airflow channels for supplying ambient air from the first inlet openings to the first outlet openings; and
    a fan mounted in the base for blowing the ambient air from the first inlet openings, through the main airflow channels and out through the first outlet openings;
    wherein the base further includes:
        second inlet openings in a side wall of the base for receiving ambient air,
        second outlet openings positioned above the fragrance support, and
        auxiliary airflow channels positioned between adjacent main airflow channels and extending between the second inlet openings and second outlet openings in a manner such that air forced through the main airflow channels results in suction of ambient air through the auxiliary airflow channels and out the second outlet openings into contact with the exposable fragrance composition.

2. An air freshener enhancer according to claim 1, wherein the auxiliary airflow channels are oriented crosswise to the main airflow channels.

3. An air freshener enhancer according to claim 1, wherein the base includes:
    a hollow lower base section having a lower end with the first input openings therein,
    a hollow upper base section mounted on top of the lower section, the upper base section including:
        a bottom wall having third openings therein,
        said side wall having said second inlet openings, and
    wherein the fan is mounted to the bottom wall of the upper base section and extends into the hollow lower base section,
    wherein the main airflow channels are connected between the third openings and the second outlet openings, and
    wherein the auxiliary airflow channels are positioned in the upper base section.

4. An air freshener enhancer according to claim 1, wherein the fragrance support includes a cup-shaped wall mounted in the base and including a fragrance support plate for mounting the exposable fragrance composition thereon.

5. An air freshener enhancer according to claim 4,
    wherein the cup-shaped wall partially defines the main airflow channels, and
    wherein the second outlet openings extend through the cup-shaped wall.

6. An air freshener enhancer according to claim 1, further including a closing arrangement for at least partially closing said first inlet openings.

7. An air freshener enhancer according to claim 6, wherein said closing arrangement includes a movable plate positioned over the first inlet openings and having openings which can be positioned one of:
    in alignment with the first inlet openings to maintain the first inlet openings in a fully open position,
    partially in alignment with the first inlet openings to maintain the first inlet openings in a partially open position, and
    completely out of alignment with the first inlet openings to completely close the first inlet openings.

8. An air freshener enhancer comprising:
    a base including:
        a fragrance support for holding an exposable fragrance composition,
        first inlet openings for receiving ambient air,
        first outlet openings positioned adjacent the exposable fragrance composition, and
        main airflow channels for supplying ambient air from the first inlet openings to the first outlet openings;
    a fan mounted in the base for blowing the ambient air from the first inlet openings, through the main airflow channels and out through the first outlet openings; and
    a height adjustment arrangement mounted in the base and connected with the fragrance support for adjusting the height of the fragrance support.

9. An air freshener enhancer according to claim 8, wherein the height adjustment arrangement includes:
    a plurality of telescoping, nested tube supports connected between the fragrance support and a wall of the base, and
    a locking arrangement for locking each tube support in an extended or retracted position with respect to another tube support.

10. An air freshener enhancer according to claim 9, wherein the locking arrangement includes recesses in the tube supports and beads in adjacent tube supports for engaging in the recesses to lock the tube supports in the extended or retracted position thereof.

11. An air freshener enhancer according to claim 9, wherein the fragrance support includes a fragrance support plate on which the exposable fragrance composition is adapted to be mounted and which is connected with one of the tube supports.

12. An air freshener enhancer according to claim 11, wherein the fragrance support plate includes one of:
    finger openings therein for grasping by a person to adjust the height of the fragrance support plate via the height adjustment arrangement, and
    a graspable member connected to the fragrance support plate for grasping by a person to adjust the height of the fragrance support plate via the height adjustment arrangement.

13. An air freshener enhancer comprising:
    a base including:
        a fragrance support for holding an exposable fragrance composition,
        first inlet openings for receiving ambient air, first outlet openings positioned adjacent the exposable fragrance composition, and main airflow channels for supplying ambient air from the first inlet openings to the first outlet openings;

a fan mounted in the base for blowing the ambient air from the first inlet openings, through the main airflow channels and out through the first outlet openings; and air reflectors mounted on the base adjacent the first outlet openings for adjusting a position at which the forced air exits the base.

14. An air freshener enhancer according to claim 1, wherein the base includes a plurality of mounting arrangements at an upper end thereof, and the air reflectors are movably mounted on the mounting arrangements.

15. An air freshener enhancer according to claim 14, wherein each mounting arrangement includes a mounting block secured to an outer surface of a sidewall of the base, and each air reflector is slidably mounted up and down on a respective mounting block, with each air reflector including an upper opening.

16. An air freshener enhancer according to claim 15,
wherein each mounting block includes an outwardly and downwardly extending outer surface and side surfaces, and wherein each air reflector includes a thin walled member having an outer wall mounted over the outer surface of the mounting block and side walls mounted over the side surfaces of the mounting block.

17. An air freshener enhancer comprising:
a base including:
a fragrance support for holding an exposable fragrance composition,
first inlet openings for receiving ambient air,
first outlet openings positioned adjacent the exposable fragrance composition, and
main airflow channels for supplying ambient air from the first inlet openings to the first outlet openings;
a fan mounted in the base for blowing the ambient air from the first inlet openings, through the main airflow channels and out through the first outlet openings; and
a cover which seats upon an upper end of the base, the cover including:
an air directional arrangement for directing forced air from the first outlet openings to the exposable fragrance composition in order to provide fragrance entrained air, and
cover openings for permitting escape of the fragrance entrained air.

18. An air freshener enhancer according to claim 17, wherein the cover openings are arranged around a 360° circle so as to permit escape of the fragrance entranced air in all directions.

19. An air freshener enhancer according to claim 17, wherein the cover includes:
a central covering wall including said cover openings,
an annular wall surrounding the central covering wall, the annular wall including the air directional arrangement, and
an annular retaining wall connected with the annular wall for mounting the cover on the upper end of the base.

20. An air freshener enhancer according to claim 19, wherein the air directional arrangement is formed by one of the following:
the annular wall having a convex shape which redirects the entrained air from the first outlet openings to the exposable fragrance composition, and
at least one curved deflector which redirects the entrained air from the first outlet openings to the exposable fragrance composition.

21. An air freshener enhancer according to claim 17, further comprising an annular collar positioned between the cover and the upper and of the base for extending the height of the cover relative to the base to enable receipt on the support of a large exposable fragrance composition.

22. An air freshener enhancer comprising:
a base including:
a fragrance support for holding an exposable fragrance composition,
first inlet openings for receiving ambient air,
first outlet openings positioned adjacent the exposable fragrance composition, and
main airflow channels for supplying ambient air from the first inlet openings to the first outlet openings; and
a fan mounted in the base for blowing the ambient air from the first inlet openings, through the main airflow channels and out through the first outlet openings;
a height adjustment arrangement mounted in the base and connected with the fragrance support for adjusting the height of the fragrance support;
wherein the base further includes:
second inlet openings in a side wall of the base for receiving ambient air,
second outlet openings positioned above the fragrance support, and
auxiliary airflow channels positioned between adjacent main airflow channels and extending between the second inlet openings and second outlet openings in a manner such that air forced through the main airflow channels results in suction of ambient air through the auxiliary airflow channels and out the second outlet openings into contact with the exposable fragrance composition; and
an outlet air adjustment arrangement formed by one of:
air reflectors mounted on the base adjacent the first outlet openings for adjusting a position at which the forced air exits the base; and
a cover which seats upon an upper end of the base, the cover including:
an air directional arrangement for directing forced air from the first outlet openings to the exposable fragrance composition in order to provide fragrance entrained air, and
cover openings for permitting escape of the fragrance entrained air.

* * * * *